United States Patent
Ding et al.

(10) Patent No.: US 7,206,634 B2
(45) Date of Patent: Apr. 17, 2007

(54) METHOD AND APPARATUS FOR OPTIMIZING CARDIAC PUMPING PERFORMANCE

(75) Inventors: Jiang Ding, Maplewood, MN (US); Yinghong Yu, Maplewood, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 727 days.

(21) Appl. No.: 10/206,131

(22) Filed: Jul. 26, 2002

(65) Prior Publication Data

US 2004/0019365 A1   Jan. 29, 2004

(51) Int. Cl.
*A61N 1/365* (2006.01)

(52) U.S. Cl. ............ 607/17; 607/4; 607/9; 607/25
(58) Field of Classification Search ............ 607/9, 607/4, 25, 17
See application file for complete search history.

(56) References Cited

U.S. PATENT DOCUMENTS

| | | | |
|---|---|---|---|
| 4,401,119 A | 8/1983 | Herpers | 607/9 |
| 4,432,362 A | 2/1984 | Leckrone et al. | 607/9 |
| 4,922,907 A | 5/1990 | Hedin et al. | 128/419 P |
| 4,928,688 A * | 5/1990 | Mower | 607/9 |
| 5,161,540 A * | 11/1992 | Mueller | 600/508 |
| 5,168,869 A | 12/1992 | Chirife | 128/419 PG |
| 5,179,949 A | 1/1993 | Chirife | |
| 5,188,106 A | 2/1993 | Nappholz et al. | 128/419 PG |
| 5,312,452 A | 5/1994 | Salo | 607/17 |
| 5,318,595 A | 6/1994 | Ferek-Petric et al. | 607/17 |
| 5,330,511 A | 7/1994 | Boute | 607/25 |
| 5,334,222 A | 8/1994 | Salo et al. | 607/17 |
| 5,372,607 A | 12/1994 | Stone et al. | 607/30 |
| 5,413,592 A | 5/1995 | Schroeppel | 607/18 |
| 5,417,717 A | 5/1995 | Salo et al. | 607/18 |
| 5,466,245 A | 11/1995 | Spinelli et al. | 607/17 |
| 5,487,752 A | 1/1996 | Salo et al. | 607/17 |
| 5,514,163 A | 5/1996 | Markowitz et al. | 607/9 |
| 5,527,347 A | 6/1996 | Shelton et al. | 607/9 |
| 5,534,016 A | 7/1996 | Boute | 607/9 |
| 5,540,727 A | 7/1996 | Tockman et al. | 607/18 |
| 5,549,650 A | 8/1996 | Bornzin et al. | 607/24 |

(Continued)

FOREIGN PATENT DOCUMENTS

EP   0474958   3/1992

(Continued)

OTHER PUBLICATIONS

Partial International Search Report in PCT/US2004/002332, 4 Pages.

(Continued)

*Primary Examiner*—Robert Pezzuto
*Assistant Examiner*—Shevon Johnson
(74) *Attorney, Agent, or Firm*—Schwegman, Lundberg, Woessner, & Kluth, P.A.

(57) ABSTRACT

A cardiac rhythm and function management device configured to automatically adjust stimulation parameters used in delivering cardiac resynchronization therapy. Mechanical contraction intervals are measured using appropriately placed accelerometers and compared with optimum values. The stimulation parameters can then be adjusted accordingly in a manner that moves the mechanical contraction intervals toward their optimum values.

18 Claims, 3 Drawing Sheets

U.S. PATENT DOCUMENTS

| | | | |
|---|---|---|---|
| 5,554,177 A | 9/1996 | Kieval et al. | 607/17 |
| 5,584,868 A | 12/1996 | Salo et al. | 607/17 |
| 5,609,612 A | 3/1997 | Plicchi et al. | 607/17 |
| 5,626,620 A | 5/1997 | Kieval et al. | 607/9 |
| 5,626,623 A | 5/1997 | Kieval et al. | 607/23 |
| 5,628,777 A | 5/1997 | Moberg et al. | 607/122 |
| 5,690,689 A | 11/1997 | Sholder | 607/24 |
| 5,700,283 A | 12/1997 | Salo | 607/17 |
| 5,713,930 A | 2/1998 | van der Veen et al. | 607/25 |
| 5,713,933 A | 2/1998 | Condie et al. | 607/28 |
| 5,716,383 A | 2/1998 | Kieval et al. | 607/9 |
| 5,749,906 A | 5/1998 | Kieval et al. | 607/9 |
| 5,800,471 A | 9/1998 | Baumann | 607/25 |
| 5,836,987 A | 11/1998 | Baumann et al. | 607/17 |
| 5,891,176 A | 4/1999 | Bornzin | 607/18 |
| 6,058,329 A | 5/2000 | Salo et al. | 607/17 |
| 6,144,880 A | 11/2000 | Ding et al. | 607/23 |
| 6,208,901 B1 | 3/2001 | Hartung | 607/23 |
| 6,223,082 B1 | 4/2001 | Bakels et al. | |
| 6,280,389 B1 | 8/2001 | Ding et al. | 600/485 |
| 6,304,777 B1* | 10/2001 | Ben-Haim et al. | 607/2 |
| 6,311,089 B1 | 10/2001 | Mann et al. | 607/30 |
| 6,351,673 B1 | 2/2002 | Ding et al. | 607/24 |
| 6,360,127 B1 | 3/2002 | Ding et al. | 607/23 |
| 6,430,439 B1 | 8/2002 | Wentkowski et al. | 607/9 |
| 6,438,421 B1 | 8/2002 | Stahmann et al. | 607/9 |
| 6,449,510 B1 | 9/2002 | Albers et al. | 607/25 |
| 6,480,742 B2 | 11/2002 | Stahmann et al. | 607/27 |
| 6,507,756 B1 | 1/2003 | Heynen et al. | 607/9 |
| 6,512,952 B2 | 1/2003 | Stahmann et al. | 607/9 |
| 6,522,921 B2 | 2/2003 | Stahmann et al. | 607/9 |
| 6,522,923 B1 | 2/2003 | Turcott | 607/27 |
| 6,542,775 B2 | 4/2003 | Ding et al. | 607/24 |
| 6,553,258 B2 | 4/2003 | Stahmann et al. | 607/9 |
| 6,597,951 B2 | 7/2003 | Kramer et al. | 607/9 |
| 6,684,103 B2 | 1/2004 | Ding et al. | 607/23 |
| 6,856,836 B2 | 2/2005 | Ding et al. | |
| 6,859,665 B2 | 2/2005 | Ding et al. | |
| 6,885,890 B2* | 4/2005 | Spinelli et al. | 607/14 |
| 6,937,901 B2* | 8/2005 | Zhu et al. | 607/27 |
| 2001/0047194 A1 | 11/2001 | Thompson et al. | 607/59 |
| 2002/0123769 A1 | 9/2002 | Panken et al. | 607/9 |
| 2002/0183795 A1 | 12/2002 | Rouw et al. | 607/9 |
| 2003/0097158 A1 | 5/2003 | Belalcazar | 607/32 |
| 2003/0100925 A1* | 5/2003 | Pape et al. | 607/17 |
| 2003/0105496 A1 | 6/2003 | Yu et al. | 607/17 |
| 2003/0144702 A1 | 7/2003 | Yu et al. | 607/17 |
| 2003/0144703 A1 | 7/2003 | Yu et al. | 607/17 |
| 2004/0078059 A1 | 4/2004 | Ding et al. | 607/25 |
| 2004/0078060 A1 | 4/2004 | Ding et al. | 607/25 |
| 2004/0147966 A1 | 7/2004 | Ding et al. | |
| 2005/0038477 A1 | 2/2005 | Kramer et al. | |
| 2005/0131472 A1 | 6/2005 | Ding et al. | |

FOREIGN PATENT DOCUMENTS

| | | |
|---|---|---|
| EP | 0970721 A2 | 1/2000 |
| WO | WO-99/58191 A1 | 11/1999 |
| WO | WO-2004011088 A1 | 2/2004 |
| WO | WO-2004069333 A2 | 8/2004 |

OTHER PUBLICATIONS

Ding, J., et al., "Method and Apparatus for Setting Pacing Parameters in Cardiac Resynchronization Therapy", U.S. Appl. No. 10/352,780, filed Jan. 28, 2003, 34 pages.

Kramer, A. P., et al., "Method and Apparatus for Adjustment of Sequential Biventricular Pacing", U.S. Appl. No. 10/742,630, filed Dec. 19, 2003, 41 Pages.

Ding, J., et al., "Cardiac Pacing Using Adjustable Atrio-Ventricular Delays", U.S. Appl. No. 11/049,181, filed Feb. 2, 2005, 35 pgs.

Ding, Jiang, et al., U.S. Appl. No. 10/615,201, filed Jul. 7, 2003, 35 pages.

Ding, Jiang, et al., "Cardiac Pacing Using Adjustable Atrio-Ventricular Delays", U.S. Appl. No. 10/615,202, filed Jul. 7, 2003, 35 pages.

Kramer, Andrew P., et al., "Automatic Selection From Multiple Cardiac Optimization Protocols", U.S. Appl. No. 10/624,458, filed Jul. 21, 2003, 49 pages.

Ritter, P., et al., "A Built-In System Based on the Peak Endocardial Acceleration (PEA) for AV-Delay Optimization in DDDR Pacing", *Pace—Pacing and Clinical Electrophysiology*, No. 5, Futura Publishing Company, Inc.,(May 1997),1567.

* cited by examiner

METHOD AND APPARATUS FOR OPTIMIZING CARDIAC PUMPING PERFORMANCE

FIELD OF THE INVENTION

This patent application pertains to methods and apparatus for the treatment of cardiac disease. In particular, it relates to methods and apparatus for improving cardiac function with resynchronization therapy.

BACKGROUND

Implantable devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised pumping performance.

Heart failure refers to a clinical syndrome in which an abnormality of cardiac function causes a below normal stroke volume that can fall below a level adequate to meet the metabolic demand of peripheral tissues. It usually presents as congestive heart failure (CHF) due to the accompanying venous and pulmonary congestion. Heart failure can be due to a variety of etiologies with ischemic heart disease being the most common. Some heart failure patients suffer from some degree of AV block or are chronotropically deficient such that their cardiac output can be improved with conventional bradycardia pacing. Such pacing, however, may result in some degree of uncoordination in atrial and/or ventricular contractions because pacing excitation from a single pacing site is spread throughout the myocardium only via the much slower conducting muscle fibers of either the atria or the ventricles, and not the specialized conduction pathways. Most pacemaker patients can still maintain more than adequate cardiac output with artificial pacing, but the diminishment in pumping efficiency may be significant in a heart failure patient whose cardiac output is already compromised. Intraventricular and/or interventricular conduction defects are also commonly found in heart failure patients and can contribute to cardiac dysfunction by causing unsynchronized contractions during intrinsic beats. Other conduction defects can occur in the atria.

In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization results in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection an intrinsic atrial contraction. Appropriate specification of these parameters is necessary in order to achieve the desired optimum coordination between the atria and the ventricles and within the ventricles, and it is this problem with which the present invention is primarily concerned.

SUMMARY OF THE INVENTION

The present invention relates to a device for delivering cardiac resynchronization therapy that is configured to automatically adjust stimulation intervals in order to achieve optimum pumping performance. In one embodiment, the interval between contractions of the left atrium and left ventricle is measured and compared with a determined or estimated optimum value, and the programmed atrio-ventricular interval used to deliver ventricular stimulation after detecting atrial depolarization is then adjusted accordingly. In another embodiment, the interval between contractions of two portions of the left ventricle is measured and compared with a determined or estimated optimum value, and the programmed biventricular offset interval between the delivery of left and right ventricular stimulation is then adjusted accordingly. The mechanical contraction intervals may be measured using appropriately placed accelerometers.

DETAILED DESCRIPTION

Figure 1:
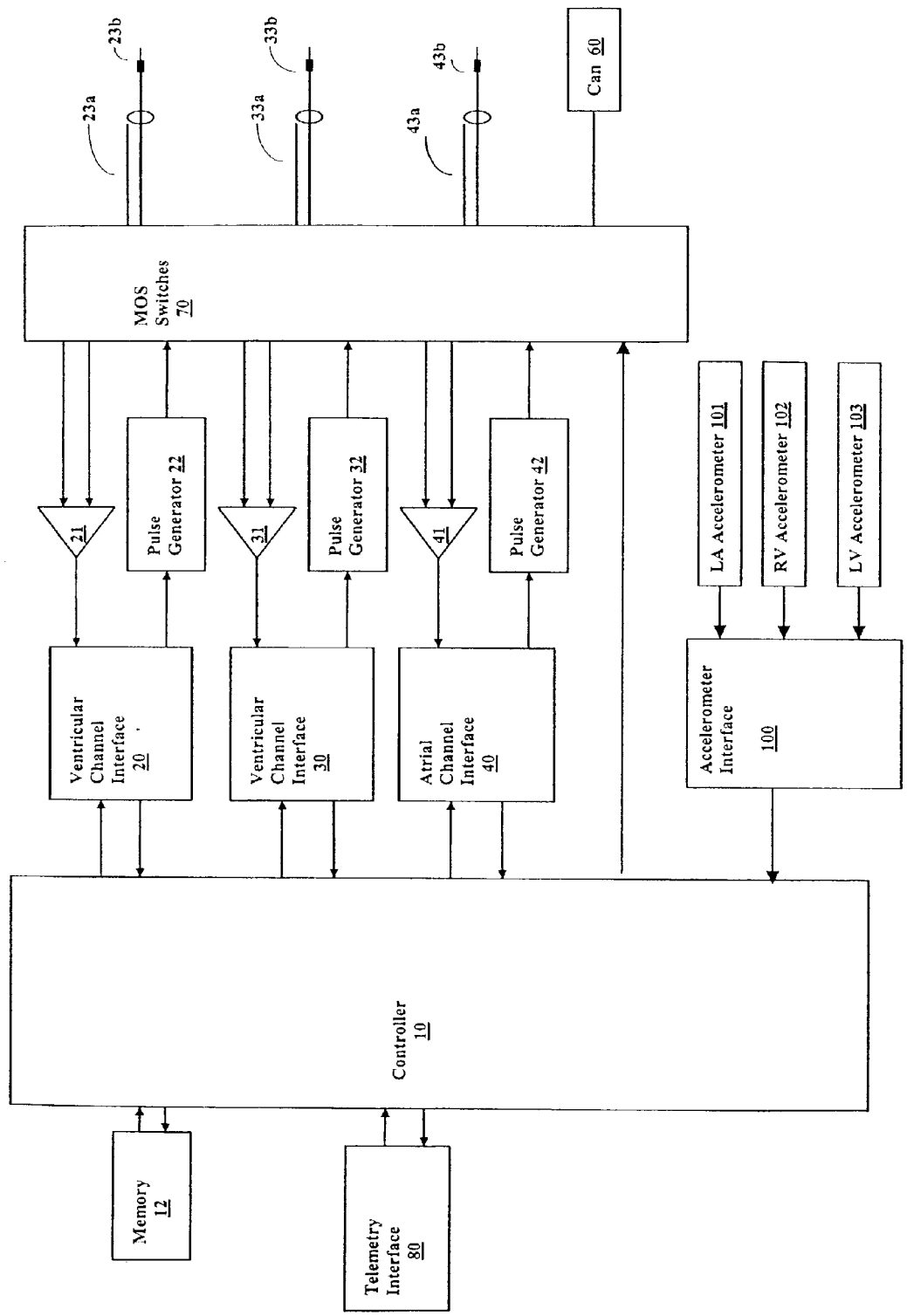
FIG. 1 is a system diagram of a pacemaker configured for biventricular stimulation and sensing.

Cardiac devices configured for delivering resynchronization therapy may be programmed with a number of different parameter settings that affect the patient's cardiac performance. In a biventricular mode, for example, stimulus pulses may be delivered to the right and left ventricles during a cardiac cycle with a specified offset interval between the pulses designed to produce a synchronized contraction within the left ventricle and between both ventricles. Because of different conduction conditions in the two ventricles, the optimum offset interval for producing a synchronized, and hence more efficient, left ventricular contraction in a given patient may vary. Another parameter that affects cardiac performance is the atrio-ventricular interval used in atrial tracking modes, which may be employed for resynchronization as well as conventional bradycardia pacing. In an atrial tracking mode, the ventricles are stimulated following an atrial intrinsic contraction or atrial pace so that diastolic filling is augmented prior to ventricular systole. Again, the optimum value for the atrio-ventricular interval varies from patient to patient.

Since the optimum values for the CRT parameters discussed above varies not only from patient to patient but may also change over time in an individual patient, it would be desirable for a cardiac resynchronization device to possess a means of automatically determining those optimum values. One method that attempts to do this in atrial tracking modes where the patient has a normal sinus rhythm is to adjust the atrio-ventricular interval and/or biventricular offset interval to values that result in the slowest intrinsic atrial rate. The body's baroreceptor feedback mechanism for regulating heart rate is thus used as a surrogate measure of cardiac output. This method can only be applied, however, in patients with intact pathways for regulating heart rate and only in stimulation modes where the atria are not paced. Also, this method may be less effective in setting optimal biventricular offset intervals. The present invention, however, represents a different approach for optimization of CRT parameters in which mechanical contractions of individual heart chambers are directly sensed. The time intervals between the contractions are measured, and the CRT parameters are then adjusted to values that result in desired mechanical contraction intervals. Such adjustments may be performed periodically or on a beat-to-beat basis. What follows is a description of an exemplary hardware platform for practicing the invention, a discussion of resynchronization therapy modes, and descriptions of exemplary embodiments.

1. Hardware Platform

Implantable cardiac devices are typically placed subcutaneously or submuscularly in a patient's chest and have leads threaded intravenously into the heart to connect the device to electrodes used for sensing and stimulation. Leads may also be positioned on the epicardium by various means. A programmable electronic controller causes the stimulus pulses to be output in response to lapsed time intervals and sensed electrical activity (i.e., intrinsic heart beats not as a result of a stimulus pulse). The devices sense intrinsic cardiac electrical activity by means of internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a stimulus pulse (a.k.a. a pace or pacing pulse when delivered in order to enforce a certain rhythm) with energy above a certain threshold is delivered to the chamber.

A block diagram of a multi-site CRT device having three sensing/stimulation channels is shown in FIG. 1. The controller of the device is made up of a microprocessor 10 communicating with a memory 12 via a bidirectional data bus, where the memory 12 comprises a ROM (read-only memory) for program storage and a RAM (random-access memory) for data storage. The controller can be implemented by other types of logic circuitry (e.g., discrete components or programmable logic arrays) using a state machine type of design, but a microprocessor-based system is preferable. The controller is capable of operating the device in a number of programmed modes where a programmed mode defines how stimulus pulses are output in response to sensed events and expiration of time intervals. A telemetry interface 80 is also provided for communicating with an external programmer.

The multiple sensing/stimulation channels may be configured to deliver univentricular, biventricular, or multi-site intra-ventricular stimulation. Illustrated in FIG. 1 is a configuration with one atrial and two ventricular sensing/stimulation channels for delivering biventricular resynchronization therapy. The atrial sensing/stimulation channel in FIG. 1 comprises ring electrode 43a, tip electrode 43b, sense amplifier 41, pulse generator 42, and an atrial channel interface 40 which communicates bidirectionally with the controller 10. The atrial sensing/stimulation channel can be used to deliver biventricular resynchronization therapy in an atrial tracking mode as well as to pace the atria if required. The device also has two ventricular sensing/stimulation channels for stimulating the ventricles that include ring electrodes 23a and 33b, tip electrodes 23b and 33b, sense amplifiers 21 and 31, pulse generators 22 and 32, and ventricular channel interfaces 20 and 30. Each of the atrial and ventricular channels thus includes a stimulation channel made up of the pulse generator connected to the electrode and a sensing channel made up of the sense amplifier connected to the electrode. The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of stimulus pulses and/or changing the stimulus pulse amplitude. For each channel, the same electrode pair is used for both sensing and stimulation. In this embodiment, bipolar leads that include two electrodes are used for outputting a stimulus pulse and/or sensing intrinsic activity. Other embodiments may employ a single electrode for sensing and stimulation in each channel, known as a unipolar lead. A MOS switching network 70 controlled by the microprocessor is used to switch the electrodes from the input of a sense amplifier to the output of a pulse generator.

The controller 10 controls the overall operation of the device in accordance with programmed instructions stored in memory, including controlling the delivery of stimulus pulses via the stimulation channels, interpreting sense signals received from the sensing channels, and implementing timers for defining escape intervals and sensory refractory periods. The sensing circuitry of the device detects a sense, either an atrial sense or ventricular sense, when an electrogram signal (i.e., a voltage sensed by an electrode representing cardiac electrical activity) generated by a particular channel exceeds a specified detection threshold. Algorithms used in particular stimulation modes employ such senses to trigger or inhibit stimulus pulses.

Figure 2:
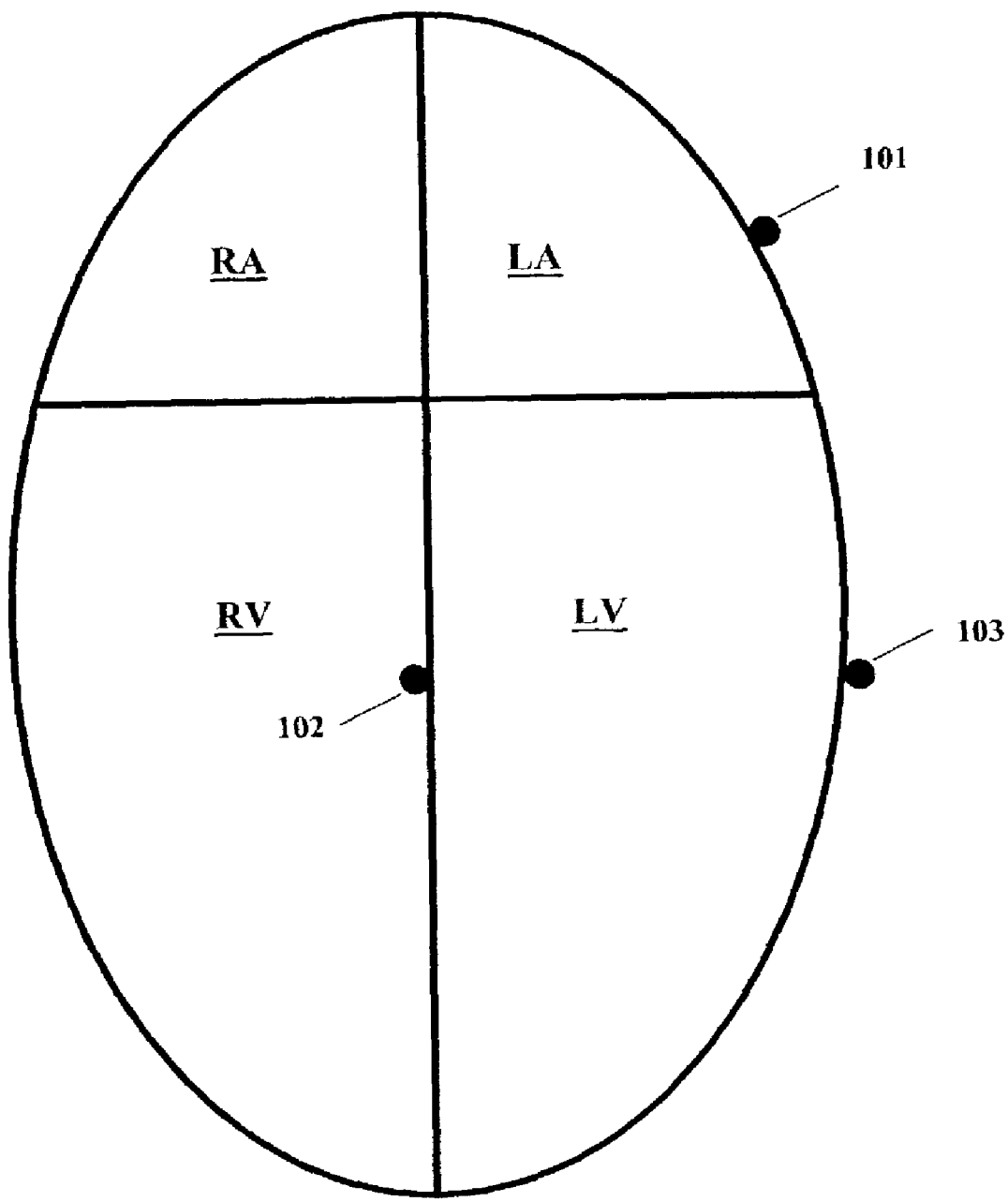
FIG. 2 shows an exemplary placement of accelerometers for measurement of mechanical contraction intervals.

Accelerometers 101, 102, and 103 are connected to the device by lead wires and designed to be affixed to walls of the left atrium, right ventricle, and left ventricle, respectively, in order to detect mechanical contractions of those chambers. FIG. 2 illustrates this placement of the accelerometers schematically where the heart chambers are labeled RA for right atrium, LA for left atrium, RV for right ventricle, and LV for left ventricle. In an exemplary implementation, the accelerometer lead wires are advanced to the heart intravenously. The right ventricular accelerometer may be affixed to the endocardial surface of the right ventricle at the septal wall, while the left atrial and ventricular accelerometers may be placed in the coronary sinus and cardiac veins, respectively, to sense movement of the free walls of those chambers. The accelerometers are interfaced to the controller by an accelerometer interface 100 that may include circuitry for threshold detection and other signal processing functions. The controller may then be programmed to measure time intervals between contractions of the septal wall and free wall of the left ventricle and between contractions of the left atrium and left ventricle. As described below, the controller can use those measured intervals to optimally adjust the atrio-ventricular and biventricular offset intervals.

2. Stimulation Modes

CRT may be most conveniently delivered in conjunction with a bradycardia pacing mode. Bradycardia pacing modes refer to algorithms used to stimulate the atria and/or ventricles when the intrinsic atrial and/or ventricular rate is inadequate due to, for example, AV conduction blocks or sinus node dysfunction. Such modes may involve either single-chamber stimulation, where either an atrium or a ventricle is stimulated, or dual-chamber stimulation in which both an atrium and a ventricle are stimulated. A bradycardia pacing mode can enforce a minimum heart rate either asynchronously or synchronously. In an asynchronous mode, the heart is stimulated at a fixed rate irrespective of intrinsic cardiac activity. There is thus a risk with asynchronous stimulation that a stimulus pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a stimulus pulse. Inhibited demand stimulation modes utilize escape intervals to control stimulation in accordance with sensed intrinsic activity. In an inhibited demand mode, a stimulus pulse is delivered to a heart chamber during a cardiac cycle only after expiration of a defined escape interval during which no intrinsic beat by the chamber is detected. If an intrinsic beat occurs during this interval, the heart is thus allowed to "escape" from stimulation by the device. Such an escape interval can be defined for each stimulated chamber. For example, a ventricular escape interval can be defined between ventricular events so as to be restarted with each ventricular sense or stimulation. The inverse of this escape interval is the minimum rate at which the device will allow the ventricles to beat, sometimes referred to as the lower rate limit (LRL).

In atrial tracking modes, another ventricular escape interval is defined between atrial and ventricular events, referred to as the atrio-ventricular interval (AVI). The atrio-ventricular interval is triggered by an atrial sense or stimulus and stopped by a ventricular sense or stimulus. A ventricular stimulus pulse is delivered upon expiration of the atrio-ventricular interval if no ventricular sense occurs before. Atrial-tracking stimulation of the ventricles attempts to maintain the atrio-ventricular synchrony that occurs with physiological beats whereby atrial contractions augment diastolic filling of the ventricles. The value of the atrio-ventricular interval for optimal preloading of the ventricles will vary with heart rate and in a manner that differs from patient to patient. If a patient has a physiologically normal atrial rhythm, atrial-tracking stimulation also allows the ventricular stimulation rate to be responsive to the metabolic needs of the body. If the atrial rhythm is too slow, the device can be configured to stimulate the atria on an inhibited demand basis. An atrial escape interval is then defined as the maximum time interval in which an atrial sense must be detected after a ventricular sense or stimulus before an atrial stimulus will be delivered. When atrial inhibited demand stimulation is combined with atrial-tracking stimulation of the ventricles, the lower rate limit interval is then the sum of the atrial escape interval and the atrio-ventricular interval.

As described above, CRT involves applying stimulus pulses to one or more heart chambers in a manner that restores or maintains synchronized contractions of the atria and/or ventricles and thereby improves pumping efficiency. Certain patients with conduction abnormalities may experience improved cardiac resynchronization with conventional single-chamber or dual-chamber bradycardia pacing. For example, a patient with left bundle branch block may have a more coordinated contraction of the ventricles with a stimulus pulse than as a result of an intrinsic contraction. More commonly, however, resynchronization therapy involves stimulating both ventricles in order to achieve better intra-ventricular and inter-ventricular synchronous contraction. Better intra-ventricular and inter-ventricular synchronization may be accomplished in a biventricular resynchronization mode by stimulating one ventricle at a specified biventricular offset interval with respect to a stimulus or sense occurring in the contralateral ventricle, the latter being stimulated with a atrial tracking mode or not stimulated at all. Which ventricle is stimulated first depends on the type of conduction disorder of the patient. For example, if the patient has left bundle branch block (LBBB), in which the left ventricle is activated later than the right ventricle, then the left ventricle is stimulated first with an atrial tracking mode.

4. Optimal Adjustment of CRT Parameters

Two factors that influence left ventricular pumping efficiency and stroke volume during a cardiac cycle are left ventricular diastolic filling volume and synchronization of contraction within the left ventricle during systole. Increased diastolic filling or preloading of the ventricle results in a stronger subsequent contraction in accordance with the Frank-Starling principle. A synchronized contraction within the left ventricle during systole results in a coordinated contraction of the ventricular septum and free wall that generates a greater pumping power and efficiency. The biventricular offset interval and the atrio-ventricular interval discussed above are thus critical parameters in determining the effectiveness of resynchronization therapy in improving a patient's cardiac performance. The atrio-ventricular interval affects the preloading of the ventricles by the atria, and the biventricular offset interval determines the degree to which the left ventricle contract in a coordinated or synchronized manner.

Clinical testing of a patient may reveal optimum values for the intervals between left atrial contraction and left ventricular contraction and between contraction of the septal wall and free wall of the left ventricle that maximize cardiac performance. For example, a patient may be given resynchronization stimulation with varying CRT parameters (i.e., atrio-ventricular and biventricular offset intervals) while pressures in the left atrium, right ventricle, and aorta are measured in order to determine when mechanical contractions occur in left atrium, right ventricle, and left ventricle, respectively. The corresponding mechanical contraction intervals can then be measured while the CRT parameters are varied. The mechanical contraction intervals that result in maximum cardiac performance, as measured by maximum left ventricular pressure change and aortic pulse pressure or other means, can then be determined along with the corresponding CRT parameters. Those CRT parameters can then be programmed into a cardiac device for delivering ventricular resynchronization therapy.

A device programmed with CRT parameters as just described may not continue to deliver optimum therapy over time, however, as conduction velocities and patterns in the patient's atria and ventricles may change. In order to maintain the optimum mechanical contraction intervals, it may therefore be necessary to modify the CRT parameters. In accordance with the invention, a cardiac device is configured to measure the mechanical contraction intervals with accelerometers as described above and to automatically adjust the CRT parameters accordingly in order to maintain the mechanical contraction intervals at their optimum values. The optimum values for the mechanical contraction intervals may be determined by clinical testing of the patient or may be estimated as nominal values. In either case, an optimum value T1 for the interval between a left atrial contraction and a left ventricular contraction and an optimum value T2 for the interval between a ventricular septal wall contraction and a left ventricular free wall contraction are programmed into the device. Either periodically or on a beat-to-beat basis, the device measures the mechanical contraction intervals with accelerometer signals, compares the measured intervals with T1 and T2, and adjusts the atrio-ventricular and biventricular offset intervals in a manner than moves the measured intervals toward T1 and T2.

In an exemplary embodiment, a device such as illustrated in FIG. 1 is configured so that one stimulation channel delivers stimuli to the right or left ventricle in accordance with a programmed mode. Accelerometers are configured for sensing mechanical contraction of the septal wall and the free wall of the left ventricle, and the controller is programmed to measure the time interval between contractions of the septal wall and the free wall of the left ventricle as sensed by the accelerometers during a cardiac cycle. Ventricular sensing channels are configured for sensing electrical activity in the right and left ventricles, with the controller programmed to stimulate one ventricle at a biventricular offset interval with respect to a sense from the contralateral ventricle. The device may be further configured with a second stimulation channel so that both ventricles receive stimuli, and either the right or left ventricle is then stimulated at the biventricular offset interval with respect to either a sense or stimulation of the contralateral ventricle. In either case, the controller is then programmed to adjust the biventricular offset interval until the measured interval between the contraction of the septal wall and the free wall of the left ventricle approximately equals a specified value T2. The specified value T2 in most cases will be set to zero, representing simultaneous contraction of the two walls of the left ventricle. The biventricular offset interval that results in the desired zero T2 value may be positive, negative, or zero.

The device may be further configured with an atrial sensing channel for sensing electrical activity in an atrium and a left atrial accelerometer for sensing mechanical contraction of the left atrium, where the controller measures the time interval between contractions of the left atrium and the left ventricle as sensed by the accelerometers during a cardiac cycle. The controller is then programmed to stimulate either the left or right ventricle in an atrial tracking mode with a specified atrio-ventricular interval between an atrial sense and a ventricular stimulus and to adjust the atrio-ventricular interval until the measured time interval between contractions of the left atrium and left ventricle approximately equals a specified value T1. The device may also use an atrial stimulation channel for pacing an atrium with a demand mode, where an atrial stimulus and a ventricular stimulus are separated by the atrio-ventricular interval.

Figure 3:
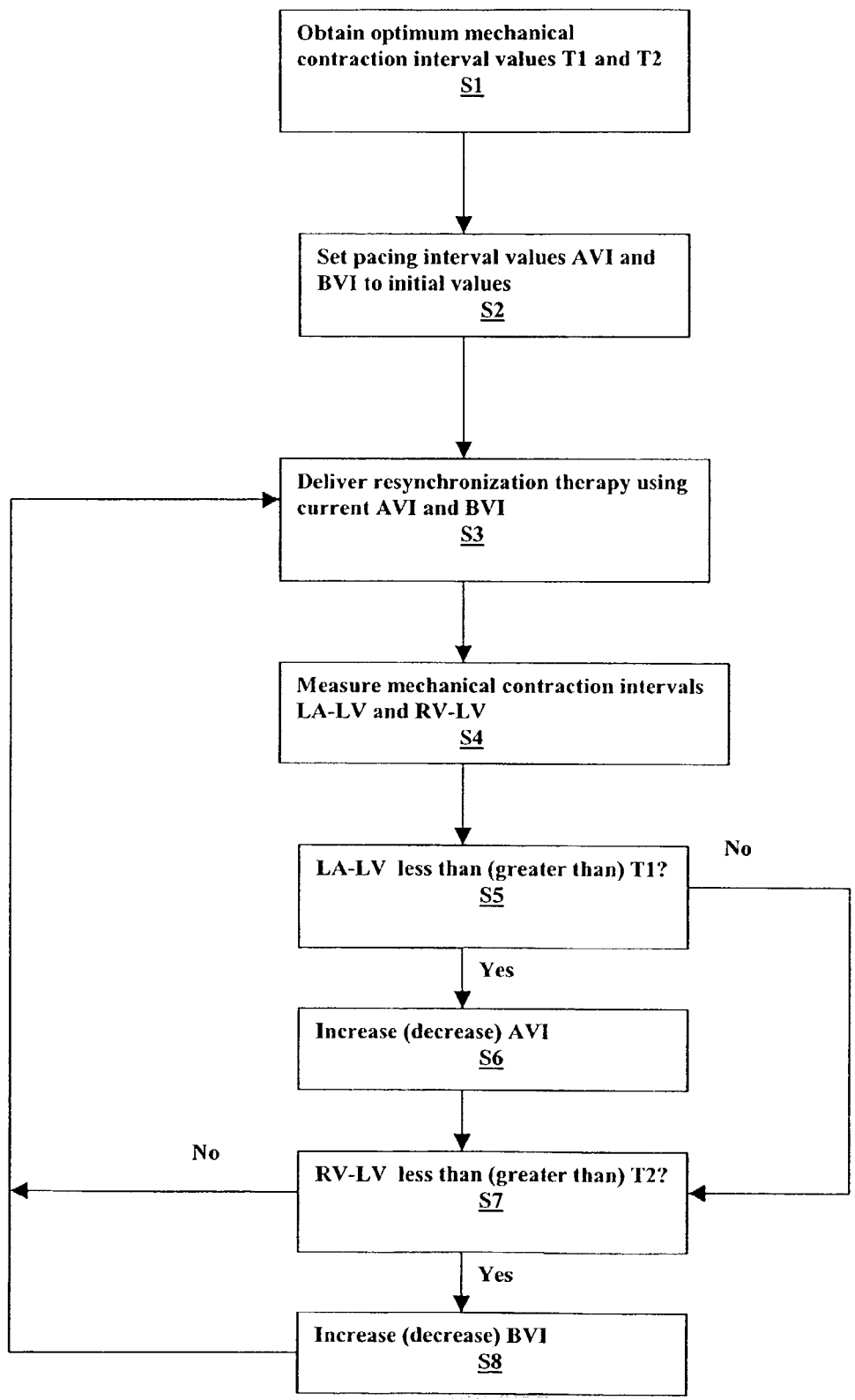
FIG. 3 illustrates an exemplary scheme for adjusting stimulation intervals based upon measured mechanical contraction intervals.

FIG. 3 illustrates the steps of an exemplary automatic interval adjustment scheme as could be implemented in the programming of the device controller. At step S1, the device is programmed with an optimum value T1 for the interval between a left atrial contraction and a left ventricular contraction and an optimum value T2 for the interval between a septal wall contraction and a left ventricular free wall contraction. At step S2, initial values for the atrio-ventricular interval AVI and the biventricular offset interval BVI are set. The device then delivers biventricular (or left ventricle-only) resynchronization therapy in accordance with a programmed mode at step S3. At step S4, the mechanical contraction intervals LA-LV and RV-LV are measured using the appropriate accelerometer signals, where LA-LV is the interval between a left atrial contraction and a left ventricular contraction and RV-LV is the interval between a septal wall contraction and a left ventricular free wall contraction. The subsequent steps then adjust the AVI and BVI values based upon the measured LA-LV and RV-LV values, either on a beat-to-beat basis or periodically. In the latter case, the LA-LV and RV-LV values may be average values obtained from a number of cardiac cycles. At step S5, the measured LA-LV value is compared with T1 and either increased or decreased as appropriate at step S6. Similarly, at step S7, the measured RV-LV value is compared with T2 and either increased or decreased as appropriate at step S8. The device then returns to step S3 and delivers resynchronization therapy with the updated stimulation intervals AVI and BVI.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A cardiac device, comprising:
an atrial sensing channel;
a first stimulation channel configurable for stimulating the right or left ventricle;
a controller for controlling the delivery of stimulus pulses through the stimulation channels in accordance with a programmed mode, wherein the controller is programmed to stimulate the right or left ventricle in an atrial tracking mode with a specified atrio-ventricular interval between an atrial sense and a ventricular stimulus;
a left atrial accelerometer adapted for contacting a wall of the left atrium in order to sense mechanical contraction of the left atrium;
a left ventricular accelerometer configurable for sensing mechanical contraction of the left ventricle;
wherein the controller is programmed to measure the time interval between sensed mechanical contractions of the left atrium and the left ventricle as sensed by the accelerometers during a cardiac cycle; and,
wherein the controller is further programmed to adjust the atrio-ventricular interval until the measured time interval between contractions of the left atrium and left ventricle equals a specified value (T1).

2. The device of claim 1 further comprising:
a ventricular sensing channel;

a right ventricular accelerometer configurable for sensing contraction of the right ventricle; and, wherein the controller is programmed to stimulate one ventricle at a biventricular offset interval with respect to a sense from the contralateral ventricle, and further wherein the controller is programmed to adjust the biventricular offset interval until the measured interval between contractions of the right and left ventricles equals a specified value (T2).

3. The device of claim 2 further comprising a second stimulation channel configurable for stimulating the right or left ventricle and wherein the controller is programmed to stimulate one ventricle at the biventricular offset interval with respect to either a sense or stimulation of the contralateral ventricle, and further wherein the controller is programmed to adjust the biventricular offset interval until the measured interval between contractions of the right and left ventricles equals a specified value (T2).

4. The device of claim 2 wherein the specified value (T2) is approximately zero.

5. The device of claim 2 wherein the biventricular offset interval may be positive, negative, or zero.

6. The device of claim 1 further comprising:

a second stimulation channel configurable for stimulating the right or left ventricle;

a right ventricular accelerometer configurable for sensing contraction of the right ventricle; and, wherein the controller is programmed to stimulate one ventricle at a biventricular offset interval with respect to stimulation of the contralateral ventricle, and further wherein controller is programmed to adjust the biventricular offset interval until the measured interval between contractions of the right and left ventricles equals a specified value (T2).

7. The device of claim 6 wherein the specified value (T2) is approximately zero.

8. The device of claim 6 wherein the biventricular offset interval may be positive, negative, or zero.

9. The device of claim 1 further comprising an atrial stimulation channel and wherein the controller is programmed to pace an atrium such that an atrial stimulus and a ventricular stimulus are separated by the specified atrio-ventricular interval.

10. A method for operating a cardiac device, comprising:

sensing electrical activity in an atrium;

delivering stimulus pulses to the right or left ventricle in an atrial tracking mode with a specified atrio-ventricular interval between an atrial sense and a ventricular stimulus;

sensing mechanical contraction of the left ventricular free wall;

sensing mechanical contraction of the left atrium;

measuring the time interval between sensed mechanical contractions of the left atrium and the left ventricle during a cardiac cycle; and, adjusting the atrio-ventricular interval until the measured time interval between contractions of the left atrium and left ventricle equals a specified value (T1).

11. The method of claim 10 further comprising:

sensing mechanical contraction of the right ventricle;

sensing electrical activity in at least one of the right and left ventricles;

stimulating one ventricle at a biventricular offset interval with respect to a sense from the contralateral ventricle; and, adjusting the biventricular offset interval until the measured interval between contractions of the right and left ventricles equals a specified value (T2).

12. The method of claim 11 further comprising stimulating both right and left ventricles, wherein one ventricle is stimulated at the biventricular offset interval with respect to either a sense or stimulation of the contralateral ventricle.

13. The method of claim 11 wherein the specified value (T2) is approximately zero.

14. The method of claim 11 wherein the biventricular offset interval may be positive, negative, or zero.

15. The method of claim 10 further comprising:

stimulating both right and left ventricles, wherein one ventricle is stimulated at a biventricular offset interval with respect to stimulation of the contralateral ventricle;

sensing mechanical contraction of the right ventricle; and, adjusting the biventricular offset interval until the measured interval between contractions of the right and left ventricles equals a specified value (T2).

16. The method of claim 15 wherein the specified value (T2) is approximately zero.

17. The method of claim 15 wherein the biventricular offset interval may be positive, negative, or zero.

18. The method of claim 10 further comprising pacing an atrium such that an atrial stimulus and a ventricular stimulus are separated by the specified atrio-ventricular interval.

* * * * *